US008672829B2

(12) United States Patent
Kaleta et al.

(10) Patent No.: US 8,672,829 B2
(45) Date of Patent: Mar. 18, 2014

(54) METHODS AND ARTICLES FOR TREATMENT OF RECTAL PROLAPSE

(75) Inventors: Richard C. Kaleta, Plymouth, MN (US); Jason Westrum Ogdahl, Minneapolis, MN (US)

(73) Assignee: AMS Research Corporation, Minnetonka, MN (US)

(*) Notice: Subject to any disclaimer, the term of this patent is extended or adjusted under 35 U.S.C. 154(b) by 1068 days.

(21) Appl. No.: 11/822,793

(22) Filed: Jul. 10, 2007

(65) Prior Publication Data

US 2008/0015614 A1 Jan. 17, 2008

Related U.S. Application Data

(60) Provisional application No. 60/819,371, filed on Jul. 10, 2006.

(51) Int. Cl.
*A61F 2/00* (2006.01)
(52) U.S. Cl.
USPC ............................................. 600/37; 606/151
(58) Field of Classification Search
USPC .................................. 600/29–32, 37; 606/151
See application file for complete search history.

(56) References Cited

U.S. PATENT DOCUMENTS

| 5,582,616 | A  | * | 12/1996 | Bolduc et al. ............... 606/143 |
| 6,332,888 | B1 |   | 12/2001 | Levy et al. |
| 6,575,897 | B1 | * | 6/2003  | Ory et al. ...................... 600/30 |
| 6,706,057 | B1 |   | 3/2004  | Bidoia et al. |
| 6,981,983 | B1 | * | 1/2006  | Rosenblatt et al. ........... 606/216 |
| 2002/0161382 | A1 |  | 10/2002 | Neisz et al. |
| 2003/0078604 | A1 | * | 4/2003  | Walshe ........................ 606/151 |

OTHER PUBLICATIONS

Furnas, David W., and Walter Birnbaum. "Interpretation of Digital Examination of the Rectum." Diseases of the Colon and Rectum 1.5 (Sep. 1958): 365-371.*

* cited by examiner

*Primary Examiner* — Charles A Marmor, II
*Assistant Examiner* — Carrie R Dorna
(74) *Attorney, Agent, or Firm* — Gregory L. Koeller

(57) ABSTRACT

Improved methods and devices for treatment of rectal prolapse are provided. A suturing console for suturing the rectal fascia at, to, or about the sacral vertebral fascia is disclosed. A method of repairing prolapsed rectum via a vaginal incision or perineal incision is also disclosed.

9 Claims, 8 Drawing Sheets

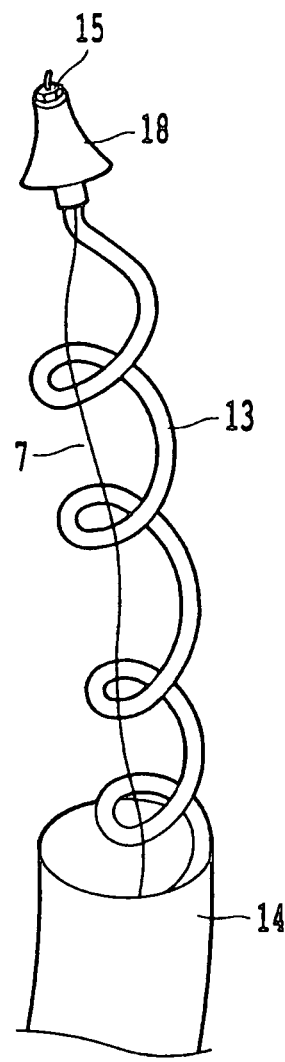
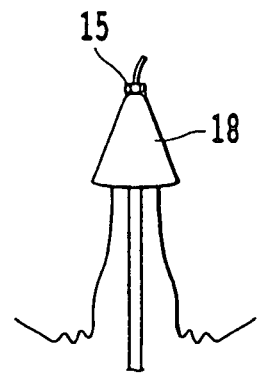
Fig. 10A
Fig. 10B

*Fig. 11A*  *Fig. 11B*

METHODS AND ARTICLES FOR TREATMENT OF RECTAL PROLAPSE

CROSS REFERENCE TO RELATED APPLICATIONS

This patent application claims priority to U.S. Provisional Application No. 60/819,371, filed Jul. 10, 2006, the entire contents of which are herein incorporated by reference.

BACKGROUND OF THE INVENTION

1. Field of the Invention

This invention relates to urogenital and gastroenteric surgery.

2. Description of the Related Art

Rectal prolapse, in its most common form, is a condition in which the rectum, the most distal portion of the colon, protrudes from the anus. In fact, three different clinical entities are often called rectal prolapse. These include full-thickness rectal prolapse, mucosal prolapse, and internal prolapse (also known as internal intussusception). The treatment of each is different.

Full thickness prolapse is the most commonly recognized type of rectal prolapse, in which the full thickness of the rectal wall protrudes through the anus. In mucosal prolapse, only the rectal mucosa protrudes. Internal intussusception is a similar condition, but the prolapsed tissue does not extend beyond the anus.

Rectal prolapse is considered uncommon, but the true incidence is not known due to underreporting. Eighty to ninety percent of patients are women, and peaks in occurrence are seen in the fourth and seventh decades of life. Certain genetic or chromosomal abnormalities, such as cystic fibrosis, have been seen to result in increased incidence of rectal prolapse in children.

As a condition predominately affecting women, rectal prolapse is often concurrent with prolapse of other pelvic floor organs. The etiology is not clear. Chronic straining during defecation, hereditary factors, and stresses due to childbirth have been implicated, as have the normal changes in the strength of pelvic and anal sphincter muscles seen with aging, neurological disease, and previous gastrointestinal or urogenital surgery. Long-standing hemorrhoidal disease is also thought to lead to certain types of rectal prolapse.

Clinically, a rectal prolapse begins as a mass protruding from the anus only after a bowel movement which retracts when the patient stands. If the disease progresses, it eventually reaches a point where it protrudes in other situations, such as sneezing and walking, and reaches a point where it does not spontaneously retract. At this point, the patient may manually replace the mass. Eventually, the mass may continue prolapsing immediately after replacement. The rectum may become incarcerated, or ulcerated, and it may be painful. Incontinence is seen due to interruption of the normal function of the anal sphincter. In addition, the exposed mucosa of the rectum constantly secretes mucous. Bleeding is commonly seen. Trauma and strangulation of the protruded mass are possible.

Rectal prolapse is generally diagnosed by physical examination. Barium studies may be indicated, as may sigmoidoscopy, to assess the rectum for additional lesions, such as tumors or ulcers.

In young patients, conservative treatment with stool softeners and suppositories. However, in adults, these medical treatments are not generally effective, and surgery is indicated.

Full thickness prolapse is treated surgically. One common surgical technique is a sigmoid resection and rectopexy. In this procedure, a portion of the colon is removed, and the remaining portion of the rectum is anchored to the sacrum.

Various options are available for the rectopexy. The Ripstein procedure incorporates the use of a nonabsorbable material, such as a Marlex mesh, to augment the fixation to the presacral fascia. The mesh stimulates scarring that serves to hold the rectum in place. A similar process using suture instead of a mesh material is also known.

This procedure involves an abdominal surgical approach, and can be performed via laparatomy or laparoscopy. Compared to other surgical options, abdominal procedures have a lower recurrence rate, but higher morbidity. Further, abdominal approaches result in scarring from the healing of abdominal incisions.

Other surgical procedures are known, including perineal approaches. Several alternatives are available, including perineal protectomy. Also known as the Altemeier Procedure, the surgeon removes the prolapsed portion of the rectum via an incision in the protruding rectum. Other perineal methods include anal encirclement, which is essentially only palliative due to complications such as chronic constipation. The Delorme mucosal sleeve resection is a perineal approach often used for small prolapses. Compared to the abdominal approach, perineal approaches have higher recurrences, but lower morbidity.

Presently available methods of treatment are not without problems. The recurrence rate for anterior resection without sacral fixation is about 7-9%, with a morbidity rate of 15-29%.

For a rectopexy without resection, the recurrence rates range from 2-10%, with morbidity rates of 3-29%. Unfortunately, continence is only improved in 50-70% of patients, and constipation may actually worsen.

When a resection is combined with a rectopexy, the recurrence rate is reduced to about 3-4%. Morbidity ranges from 4-23%. Constipation improves in 60-80% of patients, and continence improves in 35-60% of patients.

Perineal approaches have recurrence rates up to 50%, with low morbidity. Incontinence and constipation improve in about 50% of patients.

U.S. Pat. No. 6,706,057 discloses an applicator and method for a perineal approach for treating hemorrhoids and concurrent mucosal membrane rectal prolapses. The method comprises applying compression sutures or staples to trap the tissue to be excised distal to the anus, with subsequent excision of the prolapsed tissue or hemorrhoid. Such treatment is less likely to be effective for larger prolapses.

U.S. Pat. No. 6,332,888 discloses a method and apparatus for treating rectal prolapse, the method comprising the step of constricting the opening of the anus by applying sutures around the opening. The sutures are applied using a finger-guided surgical instrument with an ejectable substantially semi-circular needle. Unfortunately, this type of treatment would appear to suffer all the problems of using anal encirclement, including chronic constipation problems.

There remains a need for safe and effective methods of treating rectal prolapse.

SUMMARY OF THE INVENTION

The present invention includes surgical instruments and implantable articles for treating rectal or pelvic muscle prolapse.

The usual methods for surgically treating rectal prolapse involve either perineal approaches or abdominal approaches.

The disclosed method, however, allows for the replacement of the prolapsed rectum into its normal anatomic position without the need for abdominal incisions. Instead, the posterior fascia of the rectum is sutured to the fascia of the sacrum and coccyx via a posterior vaginal incision (in females) or via a perineal incision (in males). No abdominal incision is required, with no scarring.

Another aspect of the present invention is specially adapted instrumentation to facilitate the disclosed method of treating rectal prolapse.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 10 shows an anchor modification of the disclosed method and device.

DETAILED DESCRIPTION OF THE PREFERRED EMBODIMENTS

Figure 1:
FIG. 1 shows a rectal prolapse.

Referring now to the drawings, wherein like reference numerals designate identical or corresponding parts throughout the several views. The following description is meant to be illustrative only, and not limiting other embodiments of this invention will be apparent to those of ordinary skill in the art in view of this description.

Figure 2:
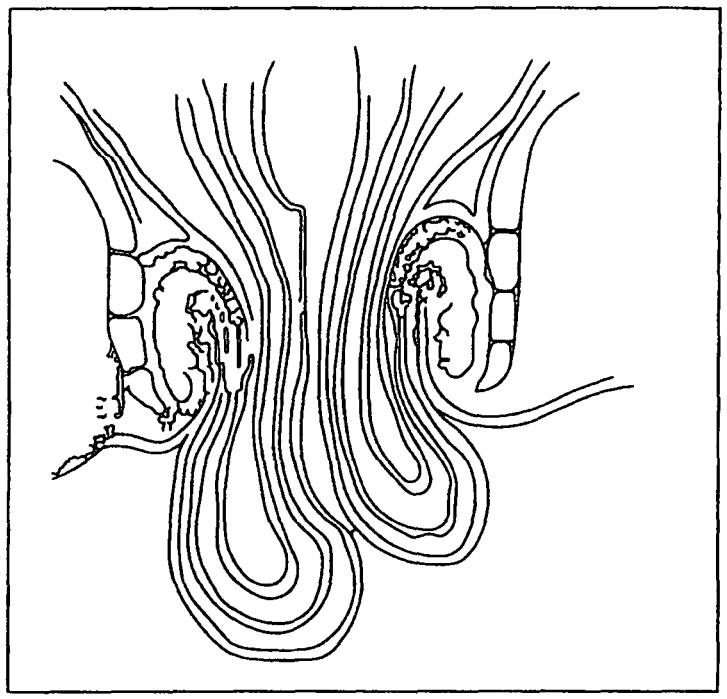
FIG. 2 shows a schematic view of a rectal prolapse.
Figure 3:
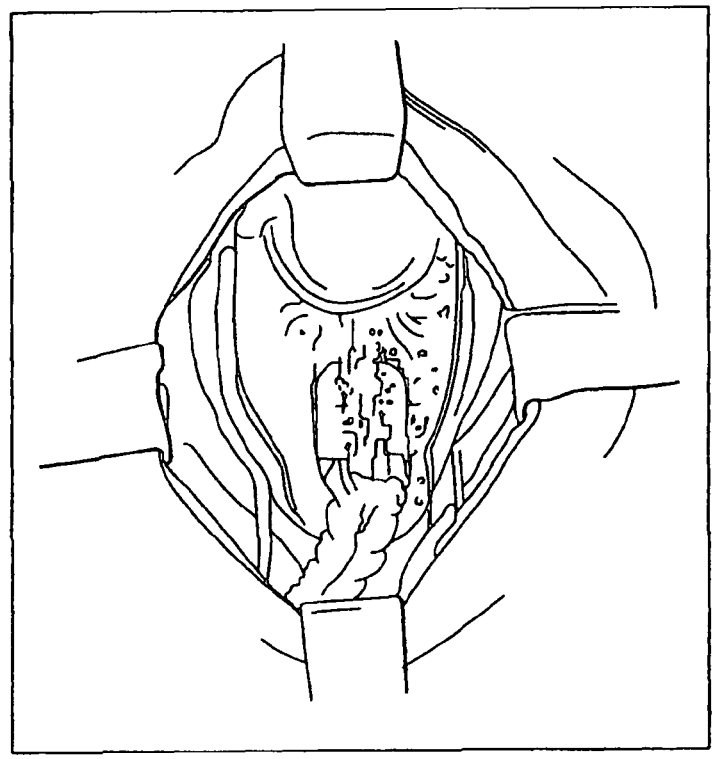
FIG. 3 shows a prior art method of treating rectal prolapse, the Marlex rectopexy.
Figure 4:
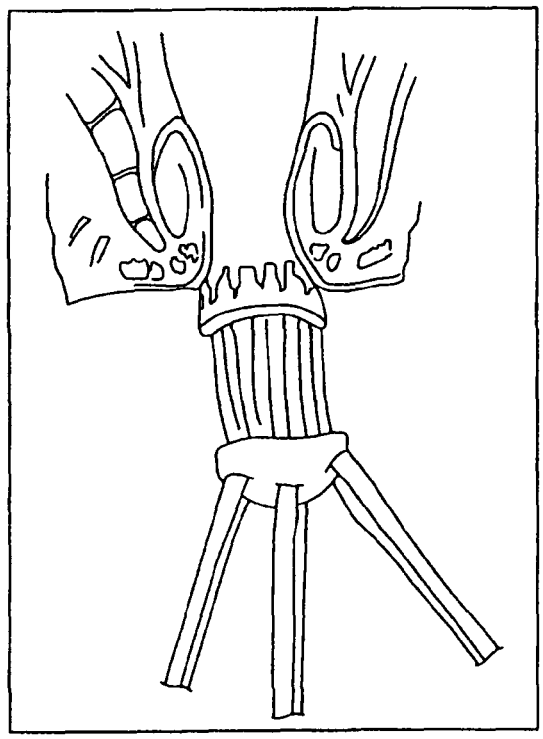
FIG. 4 shows another prior art method of treating rectal prolapse, the Altemeier procedure.

As currently commonly practiced, a rectal prolapse, illustrated in FIGS. 1 and 2, is repaired by attaching the rectum to or about or near the sacrum, as shown in FIG. 3. Other methods include resecting the exposed mass, as shown in FIG. 4.

Figure 5:
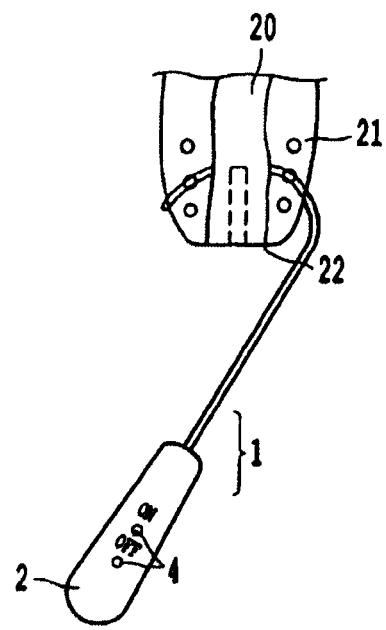
FIG. 5 shows a step in the disclosed method.

The present method is an adaptation of the procedures wherein the rectum is attached to the sacrum and coccyx. In an embodiment of the invention, the patient is placed in a modified dorsal lithotomy position with hips flexed and legs elevated in stirrups. Vaginal retraction may be required. A posterior vaginal incision is made, transversely across the vaginal apex, to create access to the peritoneal cavity. (A perineal incision is made in the male patient). The surgeon or an assistant then inserts his finger into the rectum to feel the sacrum and coccyx. After identifying these landmarks, a needle 3 is passed through the vaginal (or perineal) incision and between the rectum 20 and the sacrum 21 and coccyx 22, as shown in FIG. 5. Sutures attaching the posterior rectal fascia to sacral fascia between the first and second sacral vertebrae, between the second and third sacral vertebrae, and between the fourth and fifth sacral vertebrae are installed.

Figure 6:
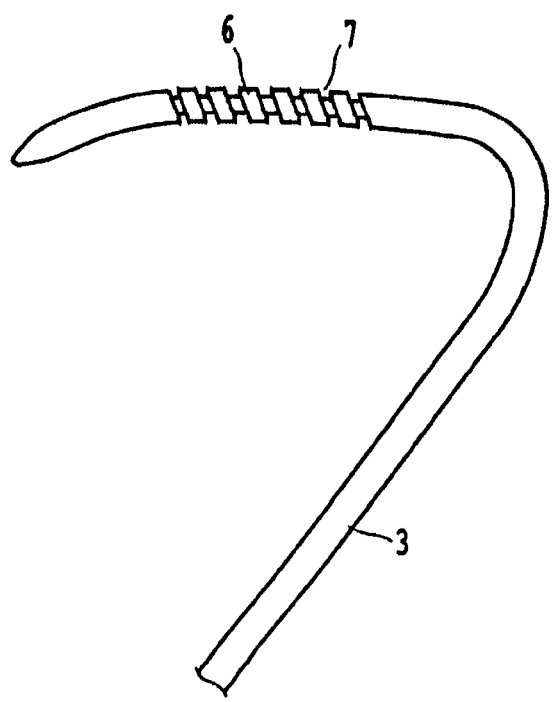
FIG. 6 shows an embodiment of the disclosed suturing console.
Figure 7A:
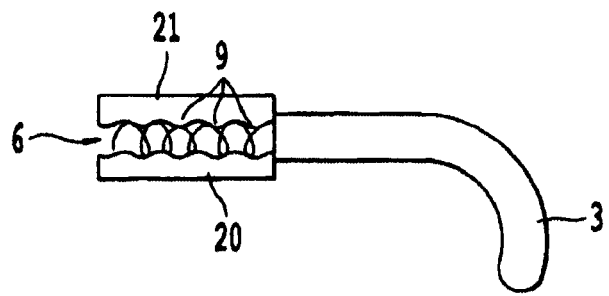
FIG. 7 shows another view of the disclosed suturing console and the disclosed method.
Figure 7B:
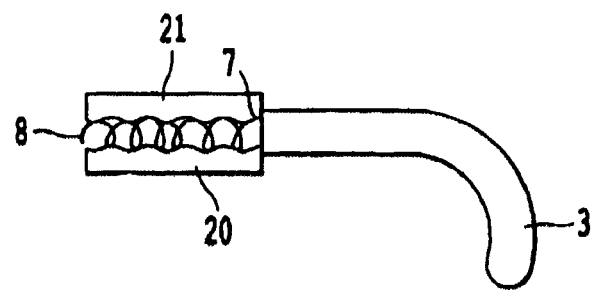
Figure 7C:
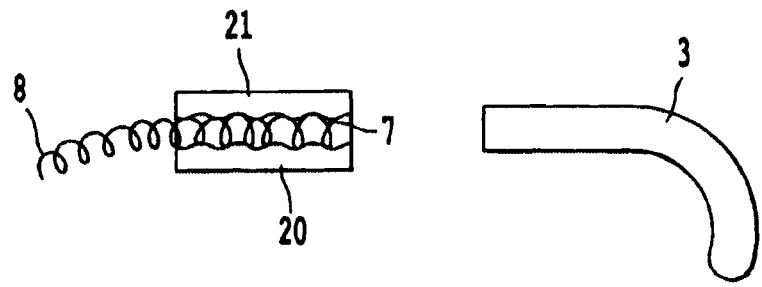

In an embodiment of the present invention, the method of correcting prolapsed rectum is effected by using a specially designed suturing console 1. Embodiments of the suturing console are shown in FIGS. 6 and 7. As can be seen from the Figures, the suturing console comprises a large modified needle 3. The large modified needle 3 of the suturing console 1 may preferably be blunt and can be of any shape, including curved or straight, as desired for the efficiency of the procedure. The suturing console 1 includes within the modified needle 3 a suture 7 with an attached sharp suturing needle 8. The end of the suture is situated near the needle tip, with an outer spring 6 situated to prevent perforation of the bowel while allowing suturing of the fascia by the sharp suturing needle 8, which is attached to the distal end of the suture 7. The sharp suturing needle 8 is preferable spring-like, to facilitate placement of sutures. Troughs 9 may be located in the protective outer spring 6 to allow for suturing with the sharp suturing needle 8 and attached suture 7. In a preferred embodiment, the suturing console 1 is placed in the proper location such that the sutures 7 may be installed. Upon placement in the proper location for attachment, the needle 3 with suture 7 is activated, and sutures 7 are installed by the spring-like needle 3 with its tip rotating through the sacral 21 and rectal fascia 20, with the spring-like needle 3 extending through the troughs 9 located in the protective outer spring 6. Upon proper placement, the end of the suture 7 is held in place, the outer spring 6 is retracted, and the suture 7 is cut and tied to secure the attachment of the sacral 21 and rectal fascia 20. This process is repeated twice more to allow for additional suture attachment points. Upon completion of the suturing process, the outer spring 6 and needle 3 are retracted into the suturing console 1 and the console 1 is removed through the vaginal incision.

In a preferred embodiment, the suturing console 1 comprises a mechanism that allows for the activation of the sharp spring-like suture needle 8 via controls 4 on the handle 2 of the suturing console 1, such as buttons or similar controls.

Figure 8A:
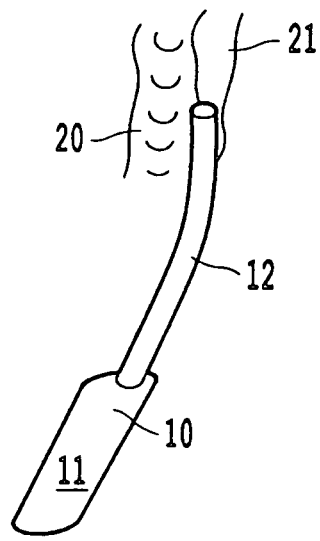
FIGS. 8 and 9 show another embodiment of the disclosed device and method.
Figure 8B:
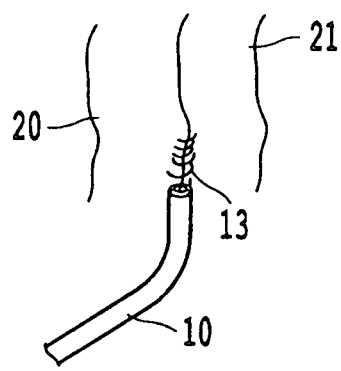
Figure 8C:
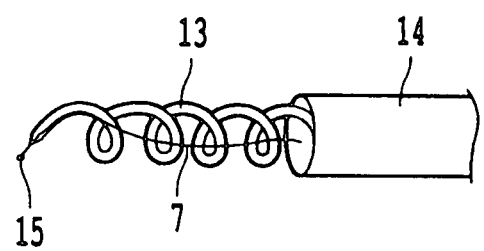
Figure 9A:
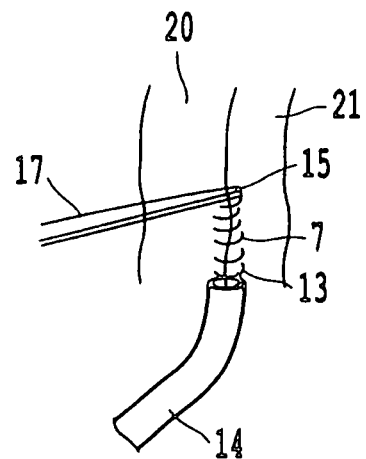
Figure 9B:
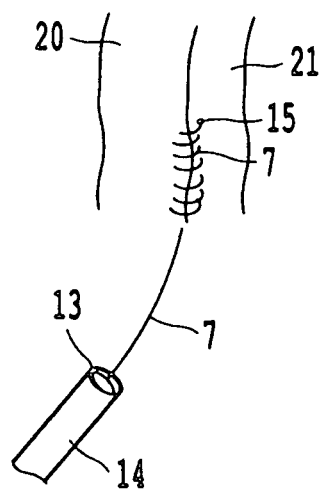

In another embodiment of the present suturing console 1, the suturing console 1 comprises a rectal tool 10 that has a tip 14, as shown in FIGS. 8 and 9. The tool 10 is placed such that the tip 14 touches both the rectal 20 and sacral fascia 21. This allows for better surgical understanding of the precise location of the sutures 7. In such a preferred embodiment, the protective outer spring 6 is not required. In a preferred embodiment, the tool 10 comprises a handle 11 and an attached tubular or housing structure 12 shaped and sized as appropriate for urogenital surgery. The tubular or housing portion 12 encloses a suture 7 with an attached sharp spring-like suture needle 13. The handle 11 may comprise some mechanism, for control of the activation of the enclosed needle 13 and suture 7. Upon proper placement, the spring-like needle 13 extends from the tip of the tubular or housing portion 12 of the rectal tool 10, and the needle 13 rotates through the rectal 20 and sacral fascia 21. Upon proper placement, the end of the suture 7 is held in place, the needle 13 is retracted into the tubular or housing portion 12, the tubular or housing portion 12 is retracted, and the suture 7 is cut and tied to secure the attachment of the sacral 21 and rectal fascia 20. This process is may be repeated as determined by the surgeon, in order to allow for additional suture attachment points and increased stability. Upon completion of each suture placement, the spring-like needle 13 is retracted into the rectal tool 10. Repetition of the process on a contralateral side of a patient may be desired, and is within the scope of the present invention. Following completion of the suturing process, the tool 10 is removed through the vaginal (or perineal) incision.

In an embodiment of the above-described method, the suture knots 15 are tied by any method known to the surgeon. Before tying a knot 15 in the first suture 7, the suture 7 is held in place by a clamp or hemostat 17 to allow for retraction of the spring-like needle 13, which further allows for retraction of the suturing console 1 or rectal tool 10 to place the next suture 7, as shown in FIG. 9. In an alternative embodiment of the described devices and method, a removable anchor 18 attached to suture 7 rests on the end of the spring-like needle 13, as shown in FIG. 10. Upon placement in a patient, the anchor eliminates the necessity for holding the suture in place, as it will engage the suture with the tissue of the patient sufficient to allow for retraction of the spring-like needle, leaving such suture in place.

In a related embodiment, the suturing tool described herein can be used for other pelvic and prolapse repairs and in connection with hysterectomies and the like.

Figure 11C:
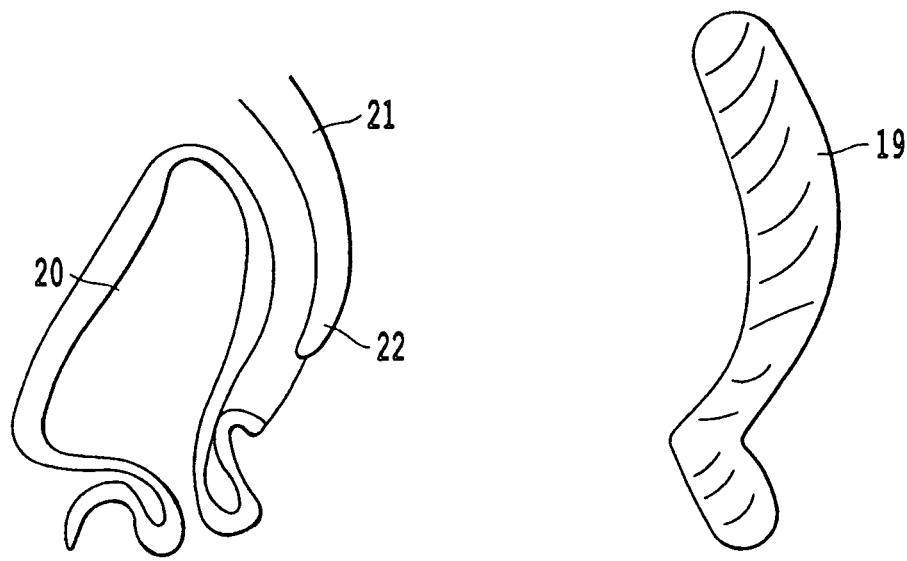
FIG. 11 shows a device used to restore the rectum to its natural geometry.
Figure 11C:
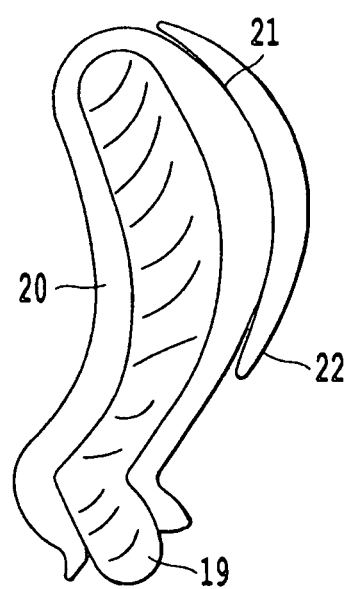

In a preferred embodiment of the present method, a rubber device 19 shaped in the natural geometry of the rectum, as shown in FIG. 11, is inserted in the prolapsed rectum 20 to assist in the replacement of the prolapsed mass into its normal anatomic position to allow suturing. This device may be of any shape and size as required to return the rectum to its proper orientation and to allow the fascia of the rectum 20 and sacral vertebrae 21 to be in close proximity.

Obviously, numerous modifications and variations of the present invention are possible in light of the above teachings. It is therefore to be understood that within the scope of the appended claims, the invention may be practiced otherwise than as specifically described herein.

The invention claimed is:

1. A method for treating rectal prolapse in a patient comprising the steps of:
   making a vaginal or perineal incision to provide access to a peritoneal cavity to attach rectal fascia tissue to sacral fascia tissue of said patient;
   inserting a tool into said vaginal or perineal incision, said tool including a needle housing and a retractable needle disposable within a length of said needle housing, said retractable needle having a distal tip and a removable distal tissue anchor, with at least one suture extending from said removable distal tissue anchor;
   positioning said retractable needle along a generally longitudinal insertion path such that said distal tip simultaneously touches said rectal tissue and said sacral tissue, and said distal tissue anchor penetrates said rectal tissue;
   actuating said tool such that said retractable needle retracts at least partially into said needle housing to leave said distal tissue anchor in said rectal tissue; and
   attaching said rectal tissue to said sacral tissue via said at least one extending suture, wherein said at least one extending suture is engaged with said rectal tissue and said sacral tissue such that said at least one extending suture connectively extends transversely between said rectal tissue and said sacral tissue, and said insertion path.

2. The method of claim 1, wherein making a vaginal or perineal incision includes making a vaginal incision comprising a posterior vaginal incision.

3. The method of claim 1, further comprising a step of identifying the sacrum and coccyx prior to attaching said rectal tissue at or to at least one sacral vertebrae.

4. The method of claim 3, wherein said sacrum and coccyx are identified by digital rectal palpation.

5. The method of claim 1, wherein said attaching said rectal tissue to said sacral tissue comprises attaching a rectal fascia to a fascia of at least one sacral vertebrae.

6. The method of claim 1, wherein said attaching said rectal tissue to said sacral vertebrae comprises at least one of attachment between the first and second sacral vertebrae, attachment between the second and third sacral vertebrae, and attachment between the fourth and fifth sacral vertebrae.

7. The method of claim 1, wherein said inserting a tool includes inserting a tool at least partially spring-like in shape.

8. The method of claim 1, wherein said at least one extending suture includes two or more extending sutures.

9. The method of claim 8, wherein said two or more extending sutures are spaced generally parallel to one another, generally transverse to said insertion path.

\* \* \* \* \*

UNITED STATES PATENT AND TRADEMARK OFFICE
CERTIFICATE OF CORRECTION

| | | |
|---|---|---|
| PATENT NO. | : 8,672,829 B2 | Page 1 of 1 |
| APPLICATION NO. | : 11/822793 | |
| DATED | : March 18, 2014 | |
| INVENTOR(S) | : Kaleta et al. | |

It is certified that error appears in the above-identified patent and that said Letters Patent is hereby corrected as shown below:

In the Specification

In Column 2, Line 19, delete "protectomy." and insert -- proctectomy. --, therefor.

Signed and Sealed this
Twenty-first Day of October, 2014

Michelle K. Lee
*Deputy Director of the United States Patent and Trademark Office*